US006454736B1

(12) United States Patent
Ludt et al.

(10) Patent No.: US 6,454,736 B1
(45) Date of Patent: Sep. 24, 2002

(54) METHOD OF FILLING A TUBE SYSTEM WITH A RINSING LIQUID AND A TUBE SYSTEM FOR USE WITH THIS METHOD

(75) Inventors: Claudia Ludt, St. Wendel (DE); Bernd Mathieu, Spiesen (DE); Hans-Jürgen Neumann, St. Wendel (DE); Thomas Pusinelli, Altenstadt (DE); Rüdiger Witt, Strande (DE)

(73) Assignee: Fresenius AG, Bad Homburg (DE)

( * ) Notice: Subject to any disclaimer, the term of this patent is extended or adjusted under 35 U.S.C. 154(b) by 0 days.

(21) Appl. No.: 09/321,999

(22) Filed: May 28, 1999

(30) Foreign Application Priority Data

May 29, 1998 (DE) .......................................... 198 24 015

(51) Int. Cl.$^7$ ............................................. A61M 37/00
(52) U.S. Cl. .................... 604/5.01; 604/6.01; 604/6.06; 604/6.16; 210/646
(58) Field of Search ................................. 210/194, 636, 210/195.1, 195.2, 195.3, 646; 604/6.02, 6.04, 6.06, 4.01, 403; 422/44–48; 494/16–21

(56) References Cited

U.S. PATENT DOCUMENTS

| 4,215,688 A | | 8/1980 | Termann et al. |
| 4,223,672 A | * | 9/1980 | Terman et al. .............. 210/782 |
| 4,227,527 A | | 10/1980 | De Frank et al. |
| 5,951,870 A | * | 9/1999 | Utterberg .................... 210/188 |
| 6,290,665 B1 | * | 9/2001 | Utterberg .................... 210/646 |

FOREIGN PATENT DOCUMENTS

| DE | 28 18 146 | 11/1979 |
| EP | 0 203 513 | 12/1986 |
| EP | 0 305 364 | 1/1998 |
| GB | 2168263 | 6/1986 |
| WO | WO 97/40869 | 11/1997 |

* cited by examiner

Primary Examiner—Angela D. Sykes
Assistant Examiner—Leslie R. Deak
(74) Attorney, Agent, or Firm—Kenyon & Kenyon

(57) ABSTRACT

A tube system comprising a blood inlet line with an arterial patient connection and a blood return line with a venous patient connection, where a rinsing liquid inlet line branches off from the blood inlet line downstream from the arterial patient connection, and a rinsing liquid return line branches off from the blood return line upstream from the venous patient connection is filled while maintaining sterility in that rinsing liquid is pumped from a rinsing liquid container through the rinsing liquid inlet line, the blood inlet line, the blood return line and the rinsing liquid return line, establishing a liquid connection between the rinsing liquid inlet line and return line. The venous patient connection is sealed liquid-tight with a venous safety cap, and the arterial patient connection is sealed liquid-tight with an arterial safety cap. The safety caps are removed from the patient connections for connecting the tube system to the patient.

17 Claims, 6 Drawing Sheets

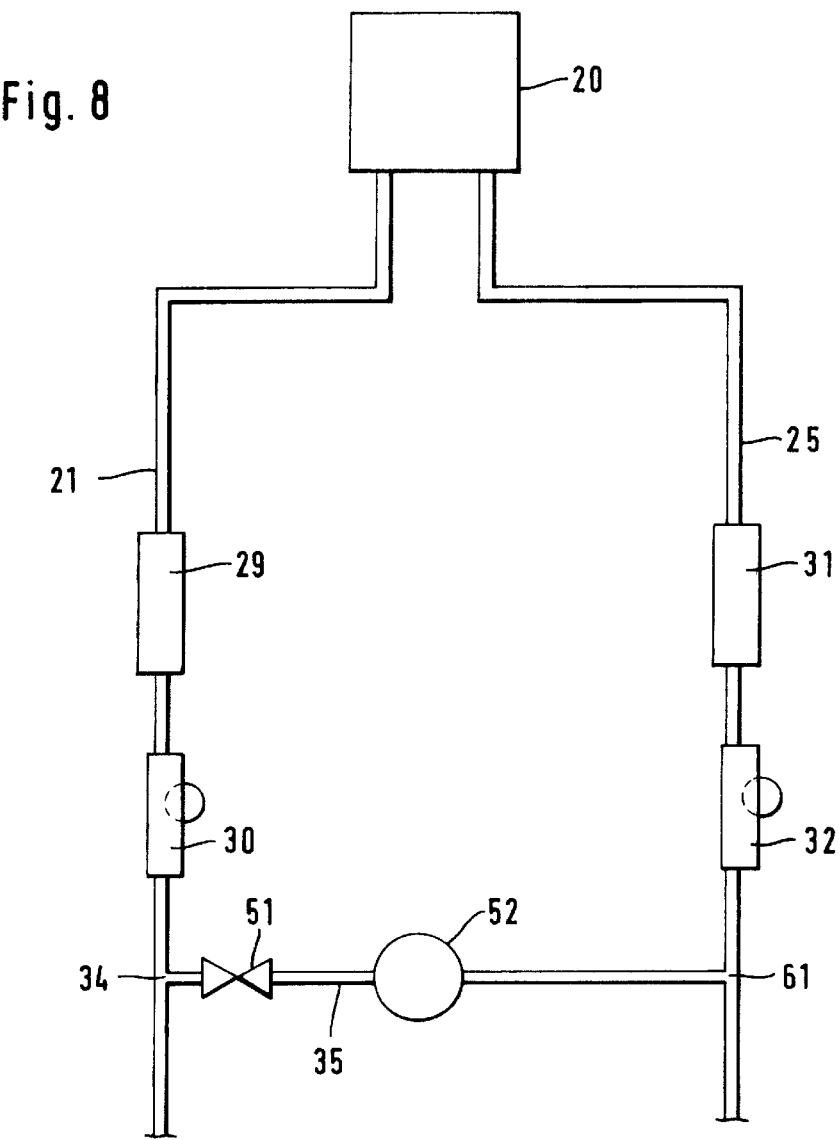
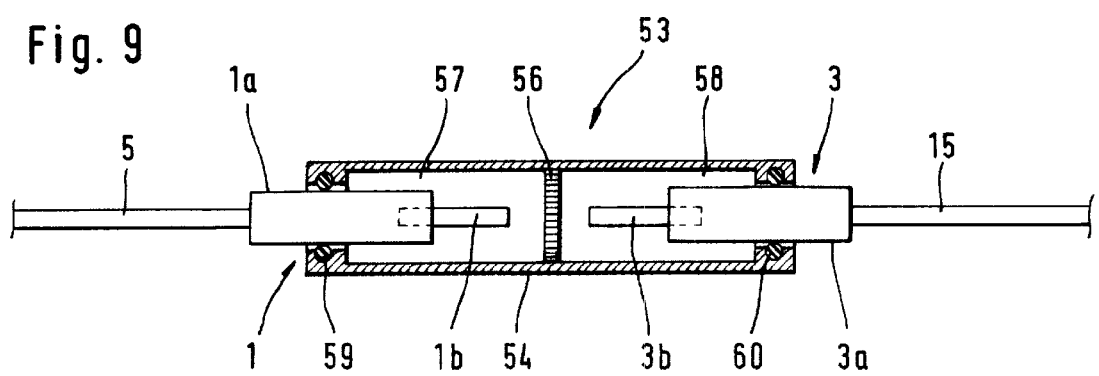

US 6,454,736 B1

METHOD OF FILLING A TUBE SYSTEM WITH A RINSING LIQUID AND A TUBE SYSTEM FOR USE WITH THIS METHOD

FIELD OF THE INVENTION

The present invention relates to a method of filling a tube system with a rinsing liquid while maintaining sterility, and a tube system for use with this method. In addition, the present invention relates to a safety cap unit for use with the tube system.

BACKGROUND INFORMATION

When treating various acute and chronic diseases, it may be necessary to perform a treatment of body fluids in an extracorporeal circulation outside the body. Such treatments are performed in hemodialysis or hemofiltration, where blood is subjected to a dialysis treatment in a dialyzer. In addition to hemodialysis or hemofiltration equipment, cell separators are also known which make it possible to separate blood of a patient into fractions. Cell separation is also performed in an extracorporeal circulation.

Since the blood treatment must be performed under sterile conditions, tube systems which are intended for a single use typically are used with current blood treatment or processing equipment. For connection to the patient, the single-use tube systems have a blood inlet line with an arterial patient connection and a blood return line with a venous patient connection.

To prepare an extracorporeal circulation, the part of the tube system intended for blood typically is rinsed with a physiological saline solution and is filled so as to admit as little air as possible by using either a non-recirculating or recirculating method of filling.

With non-recirculating methods of filling the tube system, the saline solution is drawn from a container through the blood inlet line, and then the rinsing liquid flows through the tube system and is sent through the blood return line into another container which serves to hold the used saline solution. This method has the disadvantage of a relatively high consumption of rinsing liquid.

Recirculating methods, where the supply container and the collecting container are combined, differ from the non-recirculating methods of filling the tube system. In this way, the saline solution can circulate through the tube system repeatedly without having to refill the container. For connecting the patient connections, the container has connection parts with self-sealing septa which are punctured by the cannulas of the patient connections. The advantage of the recirculating methods is the low consumption of rinsing liquid. However, they have the disadvantage that when connecting the patient connections to the container, there is the risk that the cannulas of the patient connections might be damaged. Optimally, these cannulas should be ground and sharp for puncturing the containers of the patient. European Patent Application No. 203,513 A, for example, discloses a medical bag arrangement for recirculation of the rinsing liquid.

European Patent Application No. 305,364 A describes a method of filling a tube system where the patient connections are short-circuited by a bridge, with the saline solution being supplied through a side branch of the tube system. The patient connections can be introduced into the short-circuit piece at the factory, so that the tube system is available to the user in a sterile condition. One disadvantage is that the rinsing liquid recirculates through the patient connections. This leads to a high flow resistance, especially with so-called closed systems in which the needle adapters are fixedly attached to the cannulas. Since the two patient connections are interconnected by the short-circuit piece, there is the risk, especially with complicated tube systems such as those conventionally used in cell separation, that one of the patient connections might become detached from the short-circuit piece when inserting the tube system, thus violating the sterility requirement. Another disadvantage is that one patient connection is already being exposed to an unsterile environment when the other connection is being removed from the short-circuit piece. Therefore, the tube connection must be connected to the patient very quickly.

There are also extracorporeal tube systems with regional anticoagulation. This is understood to include systems in which blood is treated with anticoagulant not inside the patient but instead only within the extracorporeal circulation. This is usually accomplished with a sodium citrate solution which is added to the blood downstream from the patient connection on the suction side. Such systems generally have a so-called "keep vein open" function which makes it possible to rinse the coagulable blood out of the cannulas and back into the patient in the event of a machine shutdown, thereby preventing coagulation inside the cannulas. Tube systems having a keep vein open function typically have rinsing liquid lines which open into the blood inlet and return lines in the immediate vicinity of the patient connections. In the case of a machine shutdown, the saline solution is supplied from a bag to the tube system through the rinsing liquid lines.

SUMMARY OF THE INVENTION

An object of the present invention is to provide a method that permits filling of a tube system, even those with regional anticoagulation, while maintaining sterility without increasing the flow resistance or exposing one of the patient connections to an unsterile environment when the other connection is ready for connection to the patient.

The present invention provides a method of filling a tube system with a rinsing liquid while maintaining the sterility of the tube system, comprising a blood inlet line with an arterial patient connection and a blood return line with a venous patient connection, where a rinsing liquid inlet line branches off from the blood inlet line downstream from the arterial patient connection, and a rinsing liquid return line branches off from the blood return line upstream from the venous patient connection. The method is characterized in that rinsing liquid is conveyed from a rinsing liquid container back into the rinsing liquid inlet line, establishing a liquid connection between the rinsing liquid inlet and return lines, with the venous patient connection being sealed liquid-tight with a venous safety cap and the arterial patient connection being sealed liquid-tight with an arterial safety cap which can be removed from the patient connections in order to connect the tube system.

The present invention also provides a tube system for use with the present method, with a blood inlet line (5) having an arterial patient connection (1) which is sealed liquid-tight with an arterial safety cap (2) which can be removed from the patient connection for connecting the tube system. A blood return line (15) has a venous patient connection (3) which is sealed liquid-tight with a venous safety cap (4) that can be removed from the patient connection for connecting the tube system. A rinsing liquid inlet line (21) branches off from the blood inlet line downstream from the arterial patient connection, and a rinsing liquid return line (25)

branches off from the blood return line upstream from the venous patient connection, with the rinsing liquid inlet line and the rinsing liquid return line being connected to a rinsing liquid container (20) that accommodates the rinsing liquid. A first cut-off device (30) is connected to the rinsing liquid inlet line downstream from the rinsing liquid container, and a second cut-off device (32) is connected to the rinsing liquid return line upstream from the rinsing liquid container. The tube system is characterized in that a short-circuit line (35) connecting the rinsing liquid inlet line (21) and rinsing liquid return line (25) is provided, with a third cut-off device (36) or a pressure control valve (51) being connected to this line.

The present invention further provides a safety cap unit for a tube system for use with the present method with an interior venous and arterial chamber (42, 43) for accommodating the venous and arterial patient connections (1, 3) of the tube system under sterile conditions, and with the interior venous chamber (43) being connected to the environment by a hydrophobic membrane (47).

With the method according to the present invention, the rinsing liquid is recirculated not through the patient connections but through the rinsing liquid lines. The rinsing liquid flows from a rinsing liquid container through the rinsing liquid inlet line, the blood inlet line, the blood return line and the rinsing liquid return line and then goes back to the rinsing liquid inlet line. Even if the safety cap becomes detached from one of the patient connections, the other patient connection is still exposed to a sterile environment.

This method can be implemented in many variants and combinations which are made possible by different tube systems. The main points of the modifications are the safety caps on the patient connections and the line configuration of the tube system in the vicinity of the rinsing liquid containers.

The term "patient connection" is understood below to refer to all means making it possible to connect the tube system to the blood vessels of the patient. The patient connections may be designed as needle adapters for attaching cannulas, but the cannulas may also be already attached to the needle adapters or they may be designed in one piece with the connections. Safety caps are hereinafter understood to refer to all devices enclosing the patient connection under sterile conditions.

In order for the safety caps to be filled completely with rinsing liquid during the rinsing operation, air in the line section of the blood inlet or return line upstream or downstream from the branch in the rinsing liquid inlet or return line is preferably let out of the safety caps. For this purpose, the safety caps have hydrophobic membranes that prevent the passage of liquid but allow air to escape.

The venous and arterial safety caps may be designed as separate parts, but it is also possible for the two safety caps to form one unit. If the venous and arterial safety caps are designed in one piece, the interior chambers of the safety caps can be vented independently of one another, but it is also possible for the air in the venous safety cap to be transferred to the arterial safety cap.

The safety cap unit for a tube system for use with the one variant of the method according to the present invention has an interior venous chamber and an interior arterial chamber to accommodate the sterile venous and arterial patient connections, respectively, where at least the interior venous chamber is connected to the environment through a hydrophobic membrane, while the safety cap unit for a tube system for use with the other variant of the method according to the present invention has two interior chambers connected to one another by a hydrophobic membrane.

BRIEF DESCRIPTION OF THE DRAWINGS

The method according to the present invention and several embodiments of the tube system for use with the method according to the present invention are explained below with reference to the figures, in which:

FIG. 8 shows another embodiment of the line configuration for establishing the flow connection between the rinsing liquid inlet and return lines; and FIG. 9 shows a schematic diagram of another embodiment of the safety cap unit for accommodating the patient connections.

DETAILED DESCRIPTION

Figure 1:
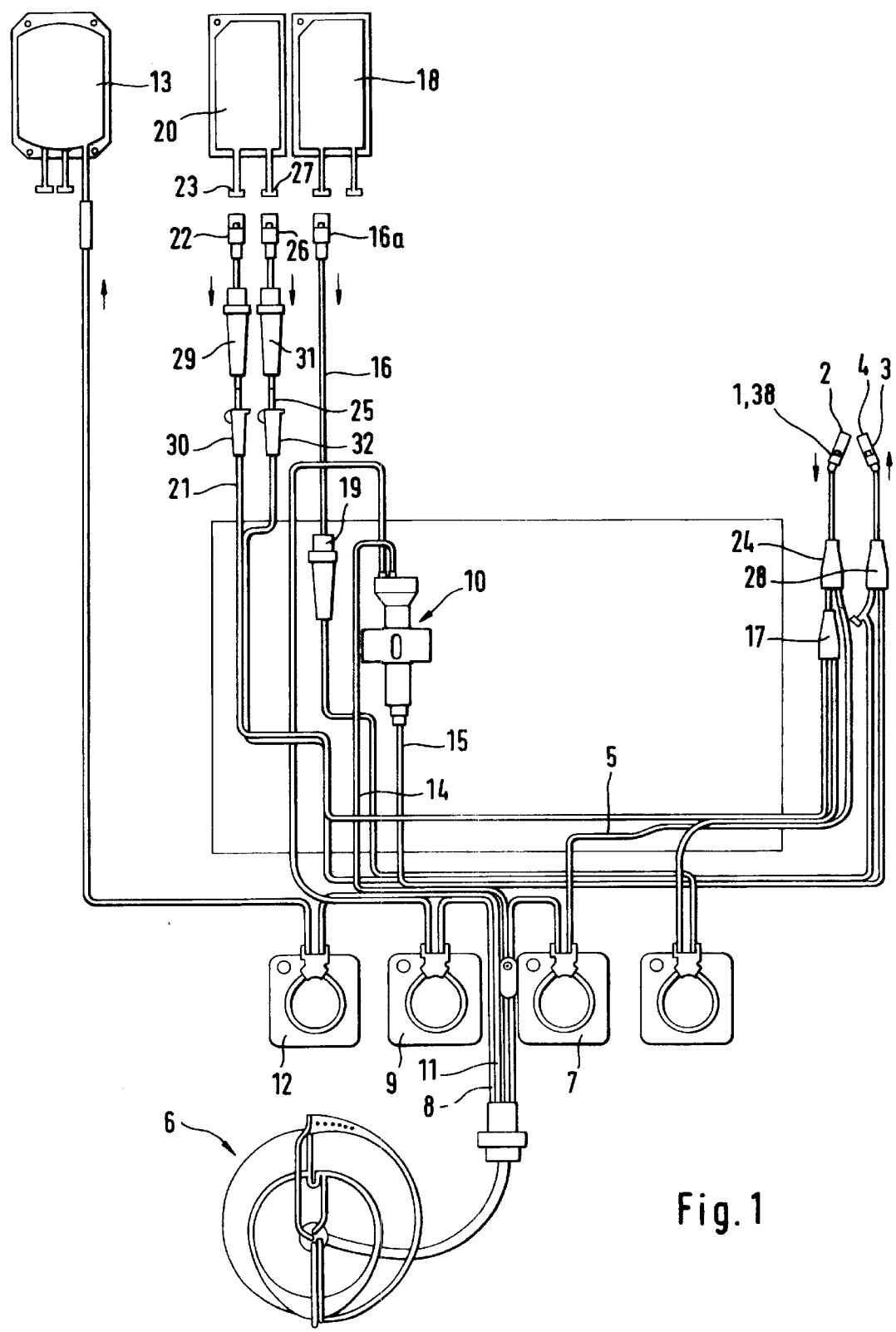
FIG. 1 shows a schematic diagram of one embodiment of a tube system for a cell separator together with the essential components of same.

FIG. 1 shows one embodiment of a tube system, referred to as a platelet set, together with components of a cell separator into which the tube system intended for a single use can be inserted.

The tube system has an arterial patient connection 1, which has a liquid-tight seal provided by an arterial safety cap 2, and a venous patient connection 3, which has a liquid-tight seal provided by a venous safety cap 4. A blood inlet line 5 is connected to the arterial patient connection 1 and to the blood inlet of a separation chamber 6. A whole blood pump 7 which pumps the blood of the patient into the separation chamber 6 is provided in the blood inlet line 5. The whole blood is separated into several fractions in separation chamber 6. Plasma depleted of platelets is removed from the separation chamber 6 through a plasma line 8 that is connected to the separation chamber 6 and is provided with a plasma pump 9. Plasma line 8 leads to the inlet of an air detector 10. The platelet fraction is removed from the separation chamber through a platelet line 11, which is connected to separation chamber 6 and to a cell pump 12, and is sent to a transfer bag 13. The erythrocyte fraction is removed through an erythrocyte line 14 connected to the separation chamber. The erythrocyte line 14 also leads to the inlet of air detector 10. The outlet of air detector 10 is connected to the venous patient connection 3 by a blood return line 15.

The tube system also has an anticoagulate, for example ACD (acid citrate dextrose), line 16 opening into blood inlet line 5 at a branch 24 near the arterial patient connection 1. At its other end, ACD line 16 has a connector 16a for connection to an ACD bag 18. A drip chamber 19 is connected to the ACD line.

The tube set also has two rinsing liquid lines opening into the blood inlet or return line near the venous and arterial patient connection, respectively. With previous tube systems, these lines served to supply rinsing liquid, in particular a saline solution from a rinsing liquid bag 20 in the case of a standstill, to rinse coagulable blood from the connections back to the patient. With the method according to the present invention, however, these lines serve to fill the tube system.

The rinsing liquid inlet line 21, having a connector 22 for connection to an outlet 23 of the bag 20, opens into blood inlet line 5 through branch 17 on a branch 24 near the arterial patient connection 1, while rinsing liquid return line 25, which has a connector 26 to the connection at an inlet 27 of the bag 20, branches off from blood return line 15 at a branch 28 near the venous patient connection 3. A first drip chamber 29 is connected to the rinsing liquid inlet downstream from the connector 22, and a first roller clamp 30 is connected downstream from this drip chamber. A second drip chamber 31 is connected to the rinsing liquid return line upstream from connector 26, and a second roller clamp 32 is connected upstream from this drip chamber.

The tube system may also include other components and is not limited to the components shown.

Figure 2:
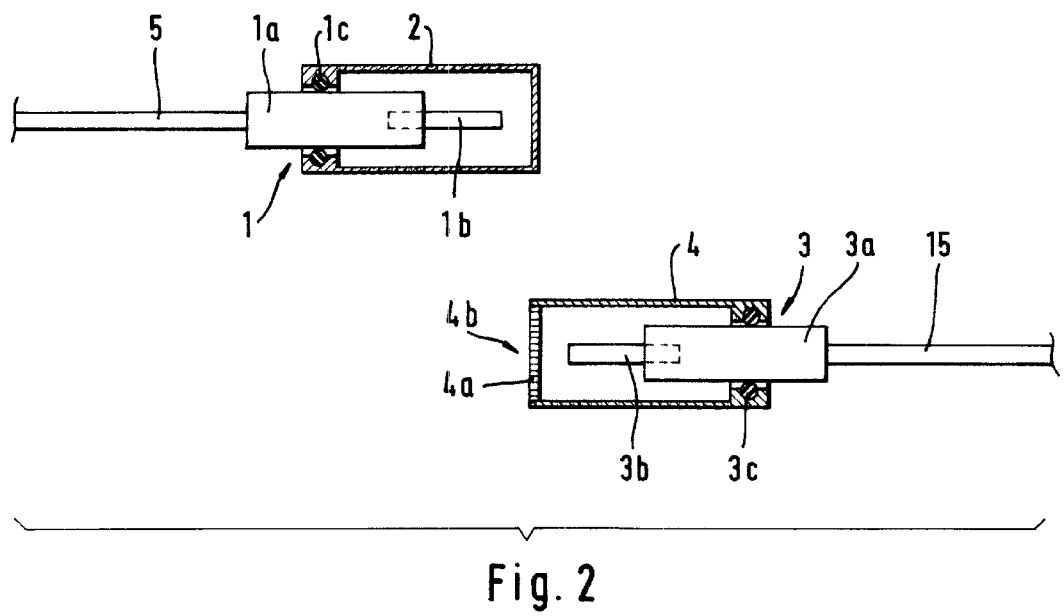
FIG. 2 shows a schematic diagram of a first embodiment of the safety caps of the tube system from FIG. 1 which close the patient connections.

FIG. 2 shows the tube ends of blood inlet line 5 and blood return line 15 together with patient connections 1, 3 which are sealed liquid-tight with safety caps 2, 4. The two patient connections 1, 3 each have a needle adapter 1a, 3a to which are attached cannulas 1b, 3b. Cylindrical safety caps 2, 4 sitting on the connection pieces 1, 3 are sealed with ring gaskets 1c, 3c with respect to needle adapters 1a, 3a under sterile connections. Venous safety cap 4 has an air outlet orifice 4b which is sealed with a hydrophobic membrane 4a, i.e., a membrane that is permeable for air but not for liquid, whereas the arterial safety cap 2 seals the arterial patient connection so it is both airtight and liquid-tight.

The tube system described with reference to FIGS. 1 and 2 is supplied as a sterile unit with the safety caps attached to the patient connections and the tube system is filled as described below.

The tube system is inserted into the cell separator with safety caps 2, 4 attached to patient connections 1, 3. With roller clamps 30, 32 closed, connectors 22, 26 of the rinsing liquid inlet and return lines 21, 25 are connected to the outlet and inlet 23, 27, respectively, of the rinsing liquid bag 20. Then, with roller clamps 30, 32 opened, operation of whole blood pump 7 is started, pumping rinsing liquid out of the rinsing liquid bag. The rinsing liquid flows through rinsing liquid inlet line 21, branch 24 and blood inlet line 5 into separation chamber 6 and back out of separation chamber 6 and into bag 20 through blood return line 15 and rinsing liquid return line 25. The rinsing liquid is then recirculated repeatedly in this closed circuit. Air in the line section of blood return line 15 downstream from branch 28 is released through hydrophobic membrane 4a of venous safety cap 4, while this line section and the safety cap are filled completely with rinsing liquid. After the end of the rinsing operation, the arterial and venous safety caps 2, 4 are removed from patient connections 1, 3, and cannulas 1b, 3b of the patient connections are punctured to connect to the blood system of the patient.

Figure 3:
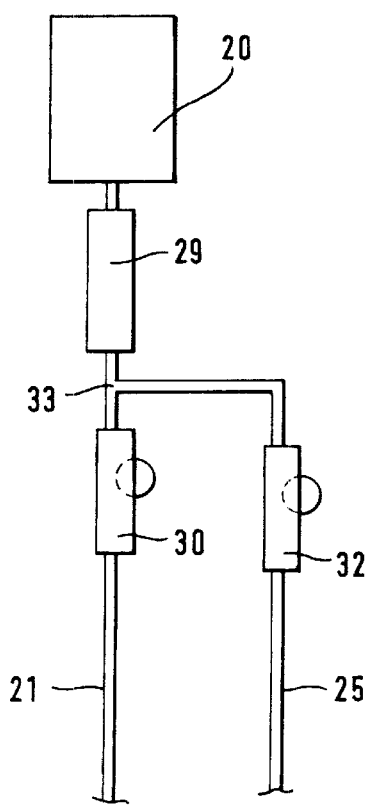
FIG. 3 shows a schematic diagram of another embodiment of the line configuration to establish a liquid connection between the rinsing liquid inlet and return lines of the tube system from FIG. 1.

FIG. 3 shows the line configuration in the area of rinsing liquid bag 20 in another embodiment of the tube system, where the parts corresponding to those in FIGS. 1 and 2 are labeled with the same reference notations. The embodiment in FIG. 3 differs from the embodiment in FIGS. 1 and 2 only in that the rinsing liquid return line opens into the rinsing liquid inlet line 21 at a connection point 33 between the first drip chamber 29 and the first roller clamp 30. A second drip chamber is eliminated with this embodiment. The rinsing liquid recirculates through rinsing liquid inlet line 21, blood inlet line 5, blood return line 15 and rinsing liquid return line 25. Since rinsing liquid does not flow through rinsing liquid bag 20, there is no risk of the rinsing liquid becoming contaminated with particles during recirculation. In comparison with the embodiment of FIGS. 1 and 2, the embodiment from FIG. 3 has the advantage that the tube system is ready to use immediately after filling. However, with the embodiment from FIGS. 1 and 2, a level is first established in drip chamber 31, which is filled completely with rinsing liquid during the filling operation, displacing the air in the rinsing liquid bag.

Figure 4:
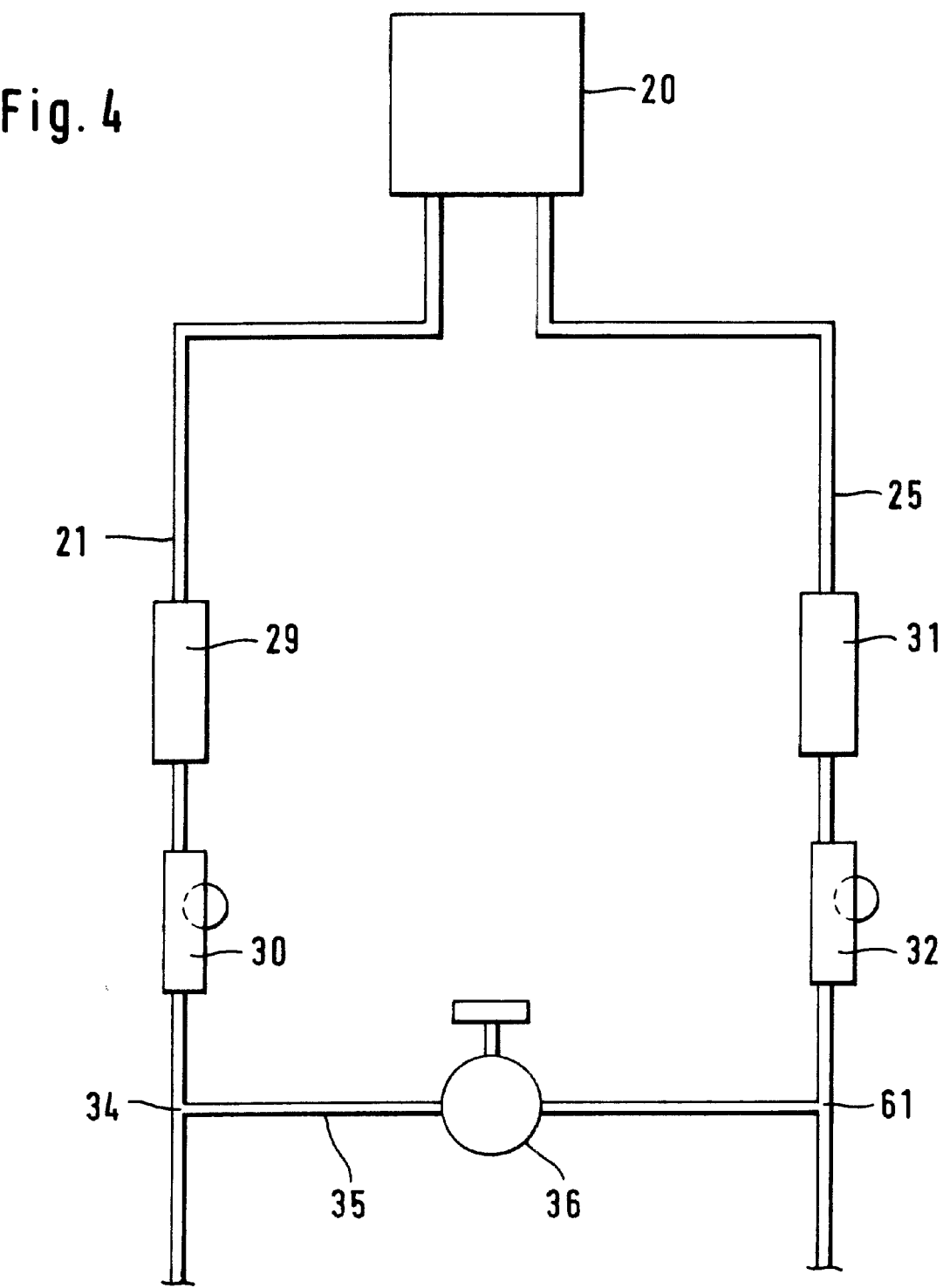
FIG. 4 shows a schematic diagram of another embodiment of the line configuration to establish the flow connection between the rinsing liquid inlet and return lines of the tube system from FIG. 1.

FIG. 4 shows the line configuration in the area of the rinsing liquid bag of another embodiment of the tube system, where the corresponding parts have again been labeled with the same reference notations. At a connecting point 61 upstream from the second roller clamp 32, a short-circuit line 35 branches off from the rinsing liquid return line 25, opening into the rinsing liquid inlet line 21 at a connection point 34 downstream from the first roller clamp 30. A third cut-off device 36, e.g., a hose clamp, is provided in the short-circuit line 35. In this embodiment, the rinsing liquid is not recirculated through bag 20 but instead through short-circuit line 35 after opening cut-off device 36.

Figure 5:
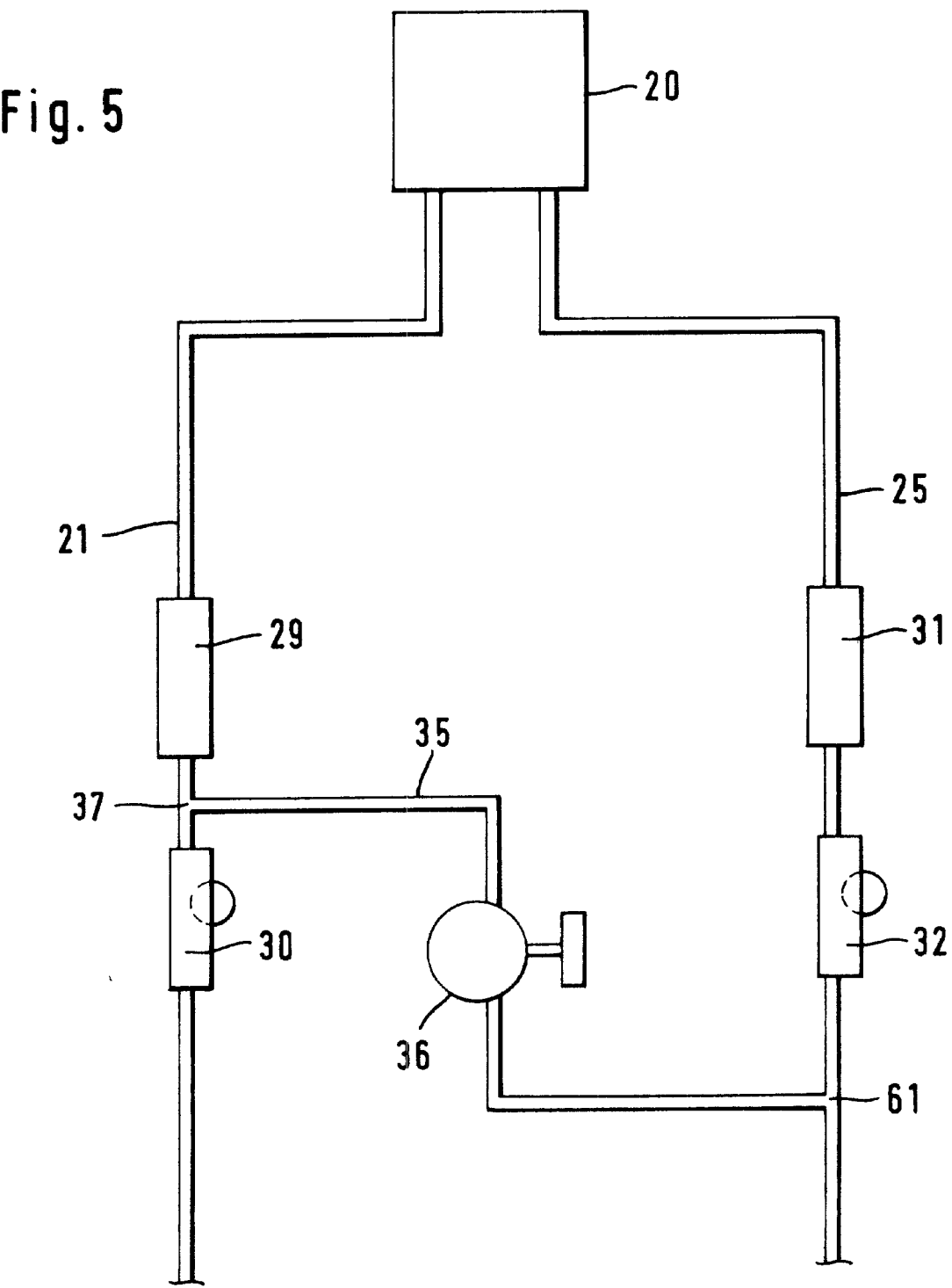
FIG. 5 shows a schematic diagram of another embodiment of the line configuration to establish the liquid connection between the rinsing liquid inlet and return lines of the tube system from FIG. 1.

FIG. 5 shows an alternative embodiment of the tube system with a short-circuit line, where the parts which correspond to those in FIG. 4 have again been provided with similar reference notations. In this embodiment, the short-circuit line 35 which branches off from the rinsing liquid return line 25 at the connection point 61 upstream from the second roller clamp 32 opens into the rinsing liquid inlet line 21 at a connecting point 37 between the first drip chamber 29 and the first roller clamp 30. Otherwise, the line configuration corresponds to that in FIG. 4. Here again, the rinsing liquid is recirculated again through the short-circuit line.

Figure 6:
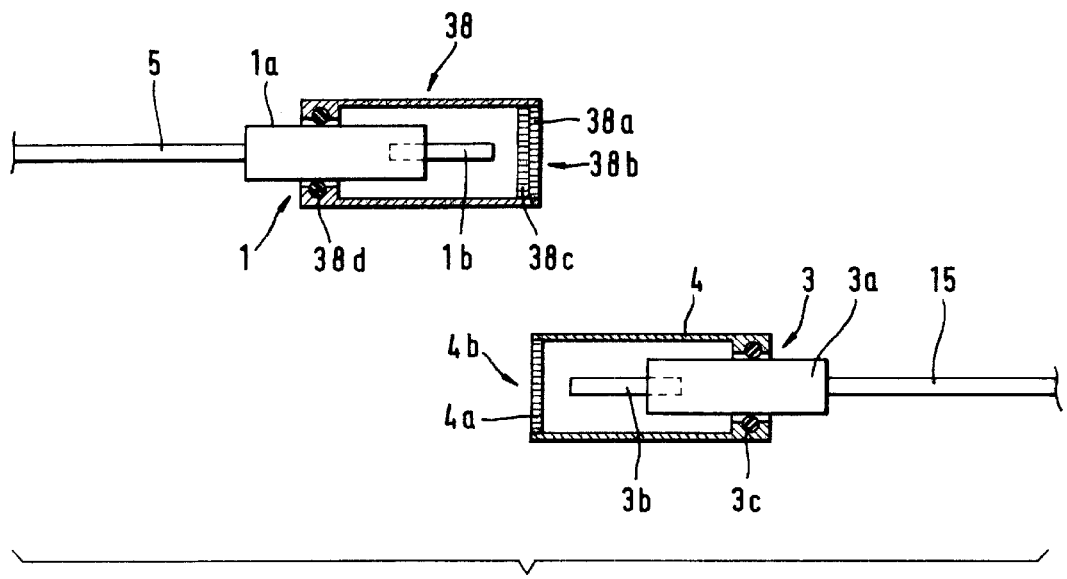
FIG. 6 shows a schematic diagram of another embodiment of the safety caps closing the patient connections with a liquid-tight seal for the tube system from FIG. 1.

FIG. 6 shows the venous and arterial safety caps in another embodiment of the tube system from FIGS. 1 and 2. However, the safety caps from FIG. 6 can also be used instead of the safety caps from FIG. 2 with the tube systems from FIGS. 3, 4 and 5. Venous safety cap 4 from FIG. 6 corresponds to that of FIG. 2. Therefore, these safety caps are also labeled with the same reference notations. However, the arterial safety cap 38 has an air outlet orifice 38b which is sealed with a hydrophobic membrane 38a, with the inside of the hydrophobic membrane being covered with a hydrophilic membrane 38c. Cylindrical safety cap 38 is sealed with a liquid-tight seal with respect to arterial patient connection 1 with a ring gasket 38d.

Figure 7:
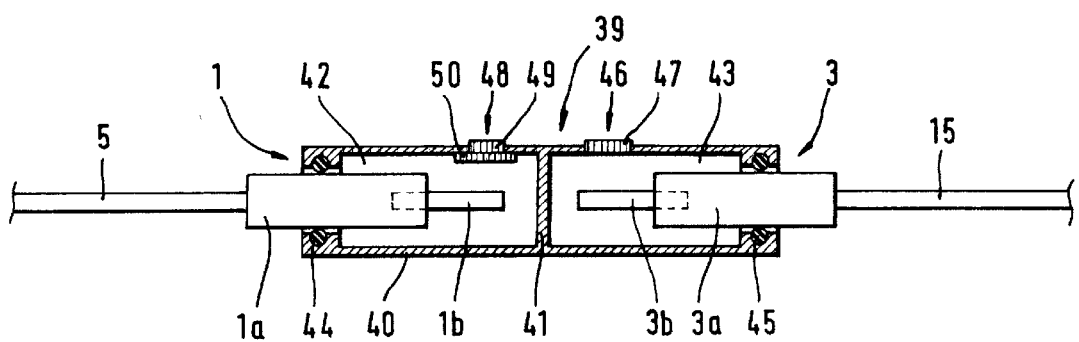
FIG. 7 shows a schematic diagram of a safety cap unit for accommodating the patient connections for the tube system from FIG. 1.

The two safety caps from FIG. 6 may also be designed in one piece. FIG. 7 shows such a safety cap unit together with the venous and arterial patient connections 1, 3 of the tube system. The safety cap unit 39 has a cylindrical body 40 which is separated by a middle partition 41 into an interior arterial chamber 42 for accommodating the arterial patient connection 1 and an interior venous chamber 43 for accommodating the venous patient connection 3. Cylindrical body 40 is sealed liquid tight with respect to patient connections 1, 3 with ring gaskets 44, 45. Interior venous chamber 43 is connected to the environment through an air outlet orifice 46 at the side, sealed with a hydrophobic membrane 47, while the interior arterial chamber 42 is connected to the environment at the side to an air outlet orifice 48 which is sealed by a hydrophobic membrane 49 whose inside is covered with a hydrophilic membrane 50.

The safety caps from FIG. 6 and the safety cap unit from FIG. 7 have the advantage in comparison with the safety caps from FIG. 2 that the line section of the blood inlet line 5 upstream from the branch 24 and the arterial safety cap 38 is filled completely with rinsing liquid. Both safety caps may also be covered with a hydrophobic or hydrophilic membrane.

The method of filling the tube system with the short-circuit line (FIG. 4 or 5) whose patient connections are sealed liquid-tight with the safety caps from FIG. 6 or the safety cap unit from FIG. 7 is described below. At the start of the rinsing operation, the rinsing liquid bag 20 is arranged at an elevated location. The first roller clamp 30 in rinsing liquid inlet line 21 is opened, while the cut-off device 36 in short-circuit line 35 and the second roller clamp 32 in the rinsing liquid return line 25 are closed. Under the influence of gravity, the rinsing liquid flows through rinsing liquid inlet line 21 into blood inlet line 5. Air in the line section of the blood inlet line 5 upstream from the branch 24 and in the arterial safety cap 38 or the interior arterial chamber 42 of the safety cap unit 39 is released from the safety cap or safety cap unit through hydrophilic membrane 38c or 50 and hydrophobic membrane 38a or 49. The rinsing liquid completely fills arterial safety cap 38 or interior arterial chamber 42 of safety cap unit 39 until it comes in contact with the hydrophobic membrane. Hydrophilic membrane 38c or 50 on the inside of the hydrophobic membrane becomes wetted in the process and thus becomes impermeable to air. Only then is operation of whole blood pump 7 started and cut-off device 36 in short-circuit line 35 opened to allow the tube system to be filled by recirculation. Air in the line section of blood return line 15 downstream from the branch 28 and in venous safety cap 3 or interior venous chamber 43 of safety cap unit 39 is released through hydrophobic membrane 4a and/or 47. Since hydrophilic membrane 38c and/or 50 of arterial safety cap 38 and/or interior arterial chamber 42 of the safety cap unit 39 have become impermeable to air due to being wetted with the rinsing liquid, this prevents the whole blood pump 7 from pumping air into blood inlet line 5.

FIG. 8 shows the line configuration in the area of the rinsing liquid bag in another embodiment of a tube system with a short-circuit line which does not require operation of a cut-off device in the short-circuit line during filling. This embodiment differs from the embodiment according to FIG. 4 in that a pressure control valve 51 is provided instead of a cut-off device 36 in short-circuit line 35, and a hydrophobic filter 52 is arranged between the pressure control valve and branching point 61. Otherwise, the line configuration corresponds to that in FIG. 4. Therefore, the corresponding parts are labeled with the same reference notations. The pressure control valve and the hydrophobic filter may also replace the cut-off device 36 from the embodiment in FIG. 5.

Pressure control valve 51 prevents rinsing liquid from entering rinsing liquid return line 25 and prevents air from being drawn in from this line. The pressure limit of the pressure control valve is designed so that the static height of the rinsing liquid bag 20 is not sufficient to open the valve, but the system pressure of blood pump 7 is sufficient. Hydrophobic filter 52 upstream from pressure control valve 51 serves to provide separation from the air in rinsing liquid return line 25. If the pressure limit of pressure control valve 51 is so high that the air can be separated reliably by a hydrophobic filter provided in the drip chamber and by the hydrophobic membrane in the venous safety cap, so that only the relatively small air volume in rinsing liquid return line 25 can reenter rinsing liquid inlet line 21, then there is the possibility of omitting hydrophobic filter 52 upstream from pressure valve 51.

With the embodiments according to FIGS. 6 and 7, hydrophilic membrane 38c or 50 can also be omitted. With such an embodiment, however, a cut-off device must be provided between the arterial and venous patient connection 1 and the branch 24 in blood inlet line 5; this cut-off device is closed before the blood pump is turned on after filling the blood inlet line under the influence of gravity and is not reopened until being connected to the patient. This cut-off device prevents air from being drawn by blood pump 7 through hydrophobic membrane 38a or 49 of the arterial safety cap 38 or interior arterial chamber 42 of safety cap unit 39, so that no air enters the line.

FIG. 9 shows another embodiment of a safety cap unit 53. Safety cap unit 53 has a cylindrical body 54 which is separated by a hydrophobic membrane 56 into an interior arterial chamber 57 to accommodate arterial patient connection 1 and an interior venous chamber 58 to accommodate the venous patient connection 3. The cylindrical body 54 is sealed liquid tight with ring gaskets 59, 60 with respect to patient connections 1, 3.

In the embodiment according to FIG. 9, interior venous chamber 58 of safety cap unit 53 is completely filled with rinsing liquid after blood pump 7 has been turned on, displacing the air in the chamber through hydrophobic membrane 56 and into interior arterial chamber 57. Although hydrophobic membrane 56 allows air to pass into blood inlet line 5, rinsing liquid does not flow through the safety cap unit.

What is claimed is:

1. A tube system comprising:
   a blood inlet line having an arterial patient connection;
   an arterial safety cap for liquid-tight sealing of the arterial patient connection, the arterial safety cap being removable from the arterial patient connection for connecting the tube system,
   a blood return line having a venous patient connection;
   a venous safety cap for liquid-tight sealing of the venous patient connection, the venous safety cap being removable from the venous patient connection for connecting the tube system;
   a rinsing liquid inlet line branching off from the blood inlet line downstream from the arterial patient connection and a rinsing liquid return line branching off from the blood return line upstream from the venous patient connection, the rinsing liquid inlet line and the rinsing liquid return line being connected to a rinsing liquid container for accommodating rinsing liquid;
   a first cut-off device being connected to the rinsing liquid inlet line downstream from the rinsing liquid container;
   a second cut-off device being connected to the rinsing liquid return line upstream from the rinsing liquid container;

a short-circuit line connecting the rinsing liquid inlet line and the rinsing liquid return line; and at least one of a third cut-off device and a pressure control valve being connected to the short-circuit line.

2. The tube system according to claim 1 further comprising a first drip chamber arranged in the rinsing liquid inlet line upstream from the first cut-off device and a second drip chamber arranged in the rinsing liquid return line downstream from the second cut-off device.

3. The tube system according to claim 2 wherein a first end of the short-circuit line branches off from an inlet line section of the rinsing liquid inlet line between the first drip chamber and the first cut-off device, and a second end of the short-circuit line branches off from a return line section of the rinsing liquid return line upstream of the second cut-off device.

4. The tube system according to claim 2 wherein a first end of the short-circuit line branches off from an inlet line section of the rinsing liquid inlet line downstream from the first cut-off device, and a second end of the short-circuit line branches off from an inlet line section of the rinsing liquid return line upstream from the second cut-off device.

5. The tube system according to claim 1 wherein the venous safety cap has an air outlet orifice sealed with a hydrophobic membrane.

6. The tube system according to claim 1 wherein the arterial safety cap has an air outlet orifice sealed by a hydrophobic membrane, an inside of the hydrophobic membrane being covered with a hydrophilic membrane.

7. The tube system according to claim 1 wherein the venous and arterial safety caps are designed in one piece having an interior venous chamber and an interior arterial chamber.

8. The tube system according to claim 1 wherein the venous and arterial safety caps are designed in one piece having an interior venous chamber and an interior arterial chamber, the interior arterial chamber being connected to the interior venous chamber through a hydrophobic membrane.

9. The tube system according to claim 1 wherein at least one of the venous and arterial patient connections has a cannula for connection to a patient, the cannula being surrounded in a sterile manner.

10. A method of filling a tube system with a rinsing liquid while maintaining sterility of the tube system, the tube system including a blood inlet line with an arterial patient connection, a blood return line with a venous patient connection, a rinsing liquid inlet line branching off from the blood inlet line downstream from the arterial patient connection, and a rinsing liquid return line branching off from the blood return line upstream from the venous patient connection, the method comprising the steps of:

conveying rinsing liquid from a rinsing liquid container into the rinsing liquid inlet line, establishing a liquid connection between the rinsing liquid inlet and the rinsing liquid return line, forming a liquid-tight seal for the venous patient connection with a venous safety cap, and forming a liquid-tight seal for the arterial patient connection with an arterial safety cap, wherein the venous safety cap and the arterial safety cap are removable from the venous and arterial patient connections.

11. The method according to claim 1 wherein the rinsing liquid return line branches off from the blood return line at a first branch, and air in a line section of the blood return line downstream from the first branch is released from the venous safety cap so that the venous safety cap is filled with the rinsing liquid.

12. The method according to claim 11 wherein the air being released from the venous safety cap is transferred from the venous safety cap to the arterial safety cap so as to establish an air-permeable but liquid-impermeable connection between the venous and arterial safety caps.

13. The method according to claim 1 wherein the conveying step includes conveying the rinsing liquid out of the rinsing liquid container and into the blood inlet line through the rinsing liquid inlet line under an influence of gravity, while air in a line section of the blood inlet line upstream from a branch in the rinsing liquid inlet line is released from the arterial safety cap so that the arterial safety cap is filled with the rinsing liquid, and sealing the blood inlet line airtight and pumping the rinsing liquid out of the rinsing liquid container by a blood pump connected to the blood inlet line.

14. The method according to claim 13 wherein the venous safety cap is filled with rinsing liquid by recirculating the rinsing liquid.

15. The method according to claim 1 wherein the establishing step includes conveying the rinsing liquid from the rinsing liquid return line through the rinsing liquid container into the rinsing liquid inlet line.

16. The method according to claim 1 wherein the establishing step includes conveying the rinsing liquid from the rinsing liquid return line into the rinsing liquid inlet line, bypassing the rinsing liquid container.

17. The method according to claim 1 wherein the conveying step includes pumping the rinsing liquid out of the rinsing liquid container using a blood pump connected to the blood inlet line.

* * * * *